US006953695B1

(12) United States Patent
Langowski

(10) Patent No.: US 6,953,695 B1
(45) Date of Patent: Oct. 11, 2005

(54) DEVICE AND METHOD FOR FLUORESCENCE CORRELATION SPECTROSCOPY, ESPECIALLY FOR MULTI-COLOR FLUORESCENCE CORRELATION SPECTROSCOPY

(75) Inventor: Jorg Langowski, Heidelberg (DE)

(73) Assignee: Deutsches Krebsforschungszentrum Stiftung des offentlichen Rechts, Heidelberg (DE)

( * ) Notice: Subject to any disclaimer, the term of this patent is extended or adjusted under 35 U.S.C. 154(b) by 0 days.

(21) Appl. No.: 09/913,575

(22) PCT Filed: Feb. 16, 2000

(86) PCT No.: PCT/DE00/00438

§ 371 (c)(1),
(2), (4) Date: Jan. 15, 2002

(87) PCT Pub. No.: WO00/49389

PCT Pub. Date: Aug. 24, 2000

(30) Foreign Application Priority Data

Feb. 18, 1999 (DE) ................................ 199 07 011

(51) Int. Cl.[7] ........................................... G01N 21/76
(52) U.S. Cl. ................ 436/172; 436/164; 436/165; 422/82.05; 422/82.08; 422/99; 422/102; 422/104; 356/244; 356/246; 250/459.1
(58) Field of Search ................ 422/82.05, 82.08, 422/99, 102, 104, 939, 942, 946, 948; 436/164, 436/165, 172; 356/244, 246; 250/459.1

(56) References Cited

U.S. PATENT DOCUMENTS 4,200,802 A    4/1980  Salzman et al. ........ 250/461 B
4,432,642 A    2/1984  Tolles ..................... 356/246
4,599,315 A *  7/1986  Terasaki et al. ......... 435/288.4
5,854,684 A * 12/1998  Stabile et al. ............ 356/440
6,396,580 B1 * 5/2002  Tewes et al. ............. 356/246

FOREIGN PATENT DOCUMENTS

| DE | 2451769 C2 | 5/1975 |
| DE | 2527770 | 1/1977 |
| DE | 3619107 A1 | 1/1987 |
| DE | 4016617 A1 | 11/1991 |
| DE | 4405375 C2 | 8/1995 |
| DE | 4405375 A1 | 11/1995 |
| DE | 19735119 A1 | 11/1999 |
| EP | 0 106 662 A2 | 4/1984 |
| EP | 0 347 579 A2 | 12/1989 |
| GB | 2 044 951 A | 10/1980 |
| JP | 0610215947 AA | 9/1986 |
| JP | 02147840 | 6/1990 |
| WO | WO 91/17832 | 11/1991 |
| WO | 95/22406 | * 8/1995 |
| WO | WO 97/19339 | 5/1997 |
| WO | WO97/45730 | 12/1997 |
| WO | 99/09393 | * 2/1999 |

* cited by examiner

Primary Examiner—Maureen M. Wallenhorst
(74) Attorney, Agent, or Firm—Steven J. Hultquist; Marianne Fuierer

(57) ABSTRACT

A device for fluorescence correlation spectroscopy, especially for multicolor fluorescence correlation spectroscopy, in which light rays are focused in a transparent medium located in a sample vessel. Such device includes a vessel holder in which at least two sample vessels with a focussing reflecting bottom are provided, and a common cover for both sample vessels which is at least partly light-transmitting. In a preferred embodiment, a plunger with a light window facing the bottom is inserted into the sample vessel, and the quantity of transparent medium is selected so that the light window of the plunger is immersed in or wetted by the medium.

14 Claims, 1 Drawing Sheet

Figure 1:
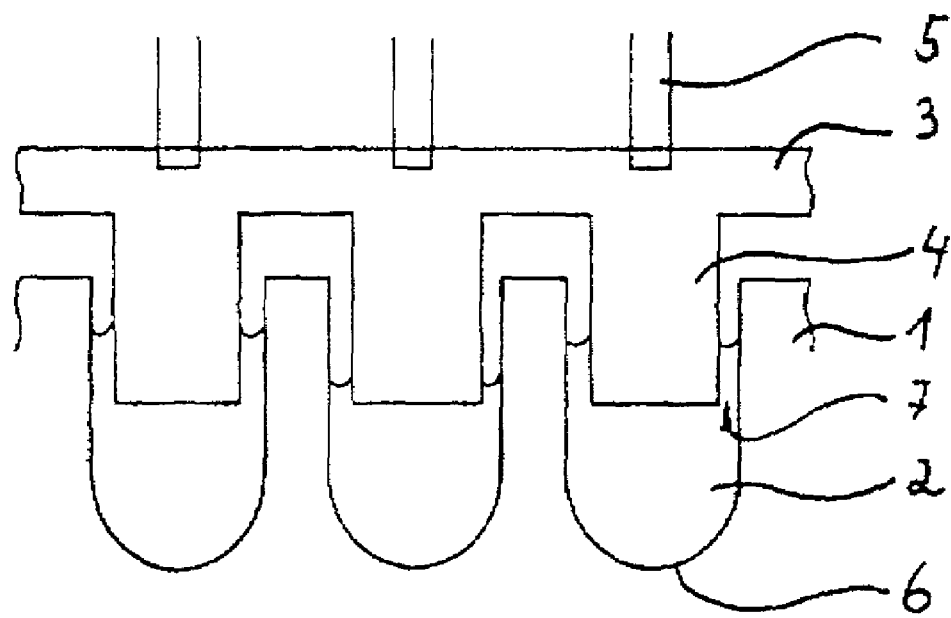

DEVICE AND METHOD FOR FLUORESCENCE CORRELATION SPECTROSCOPY, ESPECIALLY FOR MULTI-COLOR FLUORESCENCE CORRELATION SPECTROSCOPY

CROSS-REFERENCE TO RELATED APPLICATIONS

This application is filed under the provisions of 35 U.S.C. §371 and claims the priority of International Patent Application No. PCT/DE00/00438 filed Feb. 16, 2000, which in turn claims priority of German Patent Application No. 199 07 011.3 filed on Feb. 18, 1999.

The invention relates to a device and a method for fluorescence correlation spectroscopy, especially for multi-colour fluorescence correlation spectroscopy. In this method reaction partners are marked with fluorescent dyes and allowed to diffuse freely in a liquid transparent medium. Any fluctuations of the fluorescence intensity can be detected by optical methods. In particular, in multicolour fluorescence correlation spectroscopy molecular interactions are investigated with two reaction partners being marked with different fluorescent dyes. The reaction partners produce fluctuations of the fluorescence intensity as they diffuse through the transparent medium. If predominantly correlated intensity fluctuations are detected between the emission wavelengths of the two fluorophors, this indicates complex formation between the two partners.

Typically very small sample quantities are used for such investigations since the spatial volumes to be investigated are confined to a region of space in the immediate vicinity of a focus to which light rays are focussed in the transparent medium.

On the other hand, in order that fluorescence correlation spectroscopy with all its advantages can have the widest possible application, it is necessary that the implementation of the measurement method should be as uncomplicated and routine as possible.

The problem for the present invention is thus to make available a generic device and a generic method for fluorescence correlation spectroscopy, especially for multicolour fluorescence correlation spectroscopy, which on the one hand can be used for the routine implementation of measurements and on the other hand can also cope with very small sample quantities.

As a solution the invention proposes on the one hand a generic device which comprises a vessel holder in which at least two sample vessels with a focussing reflecting bottom are provided, and a common cover for both sample vessels which is at least partly transparent to light.

Such a device can also be fabricated in extremely small dimensions with sufficient precision so that very small sample volumes are available for a measurement inside such small sample vessels. In addition, the arrangement of several sample vessels in one vessel holder means that these can easily be prepared for a measurement at the same time or shortly after one another. It is also possible to provide the corresponding measurement apparatus with a holding device or transporting device for the vessel holder so that the contents of each sample vessel can be supplied for a measurement one after the other or even simultaneously without further expenditure. The arrangement according to the invention described in this manner thus, on the one hand, makes it possible to use extremely small sample volumes according to the problem and, on the other hand, allows almost continuous sample preparation or measurements.

By means of the focussing reflecting bottom it is also possible for the exciting light rays to be incident perpendicularly in the transparent medium and merely deflected to the focus inside the medium. By this means measurement errors caused by the different refractive indices and different frequencies of the incident light can be avoided or reduced to a minimum.

Preferably the sample vessel is filled so far that it reaches the cover. This ensures that any light incident in the sample vessel merely depends on the sample geometry and not on any surface stresses of the transparent medium or similar.

The complete arrangement has a relatively simple design if the sample vessels are formed by recesses in the vessel holder. With such an arrangement it is possible to construct the vessel holder in one piece and by any suitable method insert recesses therein which serve as sample vessels. In this case only the bottom of these recesses should be constructed as focussing in a fashion according to the invention.

The bottom can have a parabolic or also an elliptical shape. A hemispherical shaped bottom is also feasible within certain limits.

In order to ensure that the reflection coating has long-term durability, the bottom can be reflection-coated with a layer resistant to normal buffer solutions.

In this case the focus of the sample vessel should be selected so that it lies inside the sample vessel. With such an arrangement there is no need for complex optics which preliminarily deflect the incident light in a suitable fashion whereby in particular the risk of measurement errors caused by different angles of refraction is reduced.

Pressure equalisation can be provided at each sample vessel. Such pressure equalisation on the one hand allows each sample vessel to be filled or emptied in an arbitrary fashion and/or on the other hand ensures that assemblies such as a cover or a light window provided in the cover can be immersed in the liquid contained in the sample vessel or completely wetted by said liquid. As already explained at the beginning, this wetting or this immersion ensures that the surface direction of the liquid is not random but is determined by the surface of the cover or the surface of a light window. It is understood that such pressure equalisation can also be used independently of the other features of the device according to the invention advantageously for fluorescence correlation spectroscopy.

In the present context the term "light window" is understood as an assembly or a region of the cover through which light for fluorescence excitation is directed through the cover into an appropriate sample vessel.

For example, the cover can be formed as a plane-parallel plate which lies horizontally on the vessel holder and covers the sample vessels. In this case, however, there is usually the difficulty of completely filling the underlying vessels with the liquid medium such that at least the appropriate light windows are wetted. Relevant ways can be found by suitable methods such as seals, exact dosing and overcoming the adhesive and cohesive forces.

These problems can be avoided if there is provided on the cover a plunger which protrudes into each sample vessel. By means of the gap between the plunger and the walls of the sample vessel pressure equalisation can also take place so that the sample vessel no longer needs to be filled with the highest possible precision. Any air or too much transparent medium can be transferred to the sides. In particular, by means of simple measures such as, for example small channels or drain holes, transparent medium can be prevented from reaching neighbouring sample vessels.

Advantageously the light windows of the cover are in each case provided in the plungers.

The plunger can, on the one hand, be shaped in one piece with the cover. On the other hand it is possible for the plunger to be formed by the ends of light guide fibres which are connected to the cover and protrude through this into the sample vessels.

Advantageously the plunger is dimensioned such that between it and the sample vessel there is a gap running around the plunger. This gap is selected to be sufficiently large so that no transparent medium flows out from the sample vessel if the plunger is immersed in the sample vessel and reaches its measuring position. The space formed by this gap thus serves as a buffer which can equalise different filling quantities, especially within the limits of measurement accuracy.

It is understood that such a plunger immersing in the sample vessel can also be used advantageously with an individual sample vessel for fluorescence correlation spectroscopy regardless of the other features. Especially the sample vessel then does not need to be filled with an exactly measured filling volume. This is of great advantage especially with small sample quantities since it is all the more difficult to measure precise volumes with these. In this respect, regardless of the other features, such a plunger also makes it possible to make measurements using extremely small sample quantities with relatively large tolerances and thus under relatively complicated and rapidly executable conditions.

The invention also proposes a method for fluorescence correlation spectroscopy, especially for multicolour fluorescence correlation spectroscopy, whereby light rays are focussed in a transparent medium which is located in a sample vessel. In this case, in the sample vessel which has a focussing bottom there is inserted a plunger having a light window facing the bottom and the quantity of transparent medium is selected so that the light window of the plunger is wetted by the medium.

Advantageously the plunger is only inserted to a position above the focus in the sample vessel so that the light incident through the light window can be focussed through the bottom into the focus and there initiates a desired measurement, in the transparent medium.

The method turns out to be particularly simple if the plunger is immersed in the transparent medium. In this way sufficient wetting is ensured in any case.

If the plunger has a surface region perpendicular to the optic axis of the focussing sample vessel bottom, this ensures in a simple design fashion that light incident through the plunger is not refracted unnecessarily. By this means errors caused by light of different frequencies are avoided.

It is understood that the geometric relationships discussed in the present context such as "perpendicular", "elliptical" and "parabolic" and similar need only be selected exactly within the limits of the desired measurement accuracies for the fluorescence correlation spectroscopy. In particular, the bottom should be fabricated exactly to a fraction of the wavelengths used. Also the deviations of the cover, the plunger or the geometric position of the light window are to be selected larger or smaller according to the wavelengths used.

It is also possible to provide an opening in the wall of the sample vessel which opens into a supply pipe and/or a drain pipe for the transparent medium. These pipes can be provided for example by simple holes in the vessel holder. Likewise on the surface of the vessel holder directly below the cover there can be provided grooves which, when covered by the cover, form such channels. These simple openings or channels in a vessel holder can easily be prepared even in the smallest geometries using already known technical methods. These pipes can be used on the one hand for pressure equalisation and on the other hand for supply or removal or the transparent medium or other substances such as measuring substance or cleaning substances.

Since any design refinements such as capillary-like feeds to the focus and similar are relinquished with these simple openings, these configurations can be implemented even with the smallest sample vessel sizes. These are also conducive to fast and serial implementation of fluorescence correlation spectroscopy whereby it is understood that these openings can also be used advantageously independently of the number of sample vessels used and the presence of a cover.

Other advantages, aims and properties of the present invention are explained using the description of the appended drawings which for example show two devices for fluorescence correlation spectroscopy according to the invention. In the drawings FIG. 1 is a schematic section through a first device according to the invention and FIG. 2 is a schematic section through a second device according to the invention.

Figure 2:
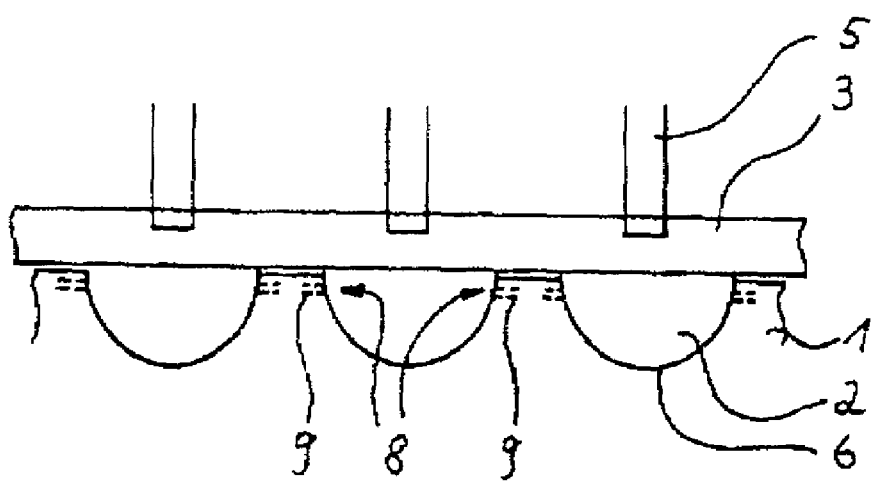

The embodiment of the invention shown in FIG. 1 has a vessel holder 1 in which recesses are inserted as sample vessels 2 (numbered as an example). This embodiment also comprises a cover 3 with transparent plungers 4 (numbered as an example) which in the covered state protrude into the sample vessels 2.

On the opposite side of the cover 3 there are provided light guides 5 (numbered as an example) through which light can be passed through the plunger 4 into the sample vessels 2 and out from said vessels. It is understood that the light guides 5 can also be provided instead of the plunger 4 and can protrude through the cover 3 into the sample vessel 2.

The bottom 6 (numbered as an example) of any one sample vessel is formed so that it is focussing and is reflection-coated on its inside with a layer resistant to normal buffer solutions.

For operation of this device the sample vessels 2 are filled with a transparent medium as required. This proceeds until after placing on the cover 3, the plungers 4 are each immersed in the transparent medium. In this respect the gap 7 (numbered as an example) between the sample vessel 2 and the plunger 4 is used for pressure equalisation and as an intermediate store for excess transparent medium.

Since the lower side of the plunger 7 has a surface region perpendicular to the optic axis of the focussing bottom 6 of the sample vessel and the light from the light guide 5 passes almost perpendicularly through a light window located in this surface region into the sample vessel 2, the cover 3 does not need to be positioned very exactly with respect to the sample vessel 2. Slight sidewards deviations are of no importance because of the parallel incidence of the light and the bottom 6 selected to be suitably focussing.

In the embodiment shown in FIG. 2 sample vessels 2 (numbered as an example) with focussing reflection-coated bottoms 6 (numbered as an example) are provided in a vessel holder 1. On the vessel holder 1 there lies a cover 3 with a flat underside in which the light guides 5 (numbered as an example) are inserted corresponding to the sample vessels. In addition in each sample-vessel wall there are provided openings 8 (numbered as an example) which open into supply or drain pipes 9 (numbered as an example). These are used on the one hand for pressure equalisation or overflow and in this way prevent transparent medium from passing over the sample vessel wall into other sample vessels 2 when the cover 3 is put in place. When the cover 3 is in place, these pipes 9 can also be used to exchange sample liquid or to flush the sample vessels 2.

The pipes 9 can on the one hand be prepared by holes (as shown). On the other hand, in the upper side of the vessel holder 1 there can be provided grooves which jointly with the cover 3 form the pipes 9. It is feasible to provide one of the openings 8 in the bottom region of the sample vessel 2.

The diameters of the openings 8 and the pipes 9 and their position are selected so that the sample vessels can be filled completely. As can be seen directly from FIG. 2, it is also possible to pass the light guides 5 through the cover 3 into the sample vessels 2. Then it is no longer necessary to completely fill the sample vessels 2.

What is claimed is:

1. A device for fluorescence correlation spectroscopy, comprising a vessel holder in which at least two sample vessels with a focussing reflection-coated bottom are provided, and a transparent medium in each sample vessel and a common cover for both sample vessels which is at least partly transparent to light, wherein light rays impinging upon the transparent medium located in each sample vessel are reflected and focussed by the focussing reflective-coated bottom of said sample vessel to a focal point within said sample vessel.

2. The device according to claim 1, wherein the sample vessels are formed by recesses in the vessel holder.

3. The device according to claim 1, wherein the common cover comprises at least two light windows for directing the impinging light rays into each sample vessel, wherein said light windows are wetted by or immersed in the transparent medium in the sample vessel.

4. The device according to claim 3, wherein said light windows are formed by plungers that each protrude into a sample vessel.

5. The device according to claim 4, wherein at least one plunger has dimensions such that between the plunger and the sample vessel there remains a gap surrounding the plunger for pressure equalization within the vessel.

6. The device according to claim 4, wherein at least one plunger has a surface region perpendicular to an optic axis of the focussing bottom of the sample vessel.

7. The device according to claim 6, wherein the impinging light rays are aligned perpendicular to said surface region of the plunger.

8. The device according to claim 4, each plunger protrudes into the sample vessel to a position above the focal point within said sample vessel.

9. The device according to claim 1, wherein a wall of each sample vessel has an opening which opens into a supply and/or drain pipe for the transparent medium.

10. A method for fluorescence correlation spectroscopy, comprising:
providing a sample vessel having a reflecting and focussing bottom and containing a transparent medium therein; and
impinging light rays upon the transparent medium located in the sample vessel,
wherein the impinging light rays are reflected and focussed by the reflecting and focussing bottom of said sample vessel to a focal point within said sample vessel.

11. The method according to claim 10, wherein the impinging light rays are directed into said sample vessel through a light window that is wetted by or immersed in the transparent medium.

12. The method according to claim 11, wherein said light window is formed by a plunger protruding into the sample vessel.

13. The method according to claim 12, wherein the plunger protrudes into the sample vessel to a position above the focal point within sample vessel.

14. The method according to claim 12, wherein the plunger has a surface region perpendicular to an optic axis of the bottom of the sample vessel, and wherein the impinging light rays are aligned perpendicular to the said surface region of the plunger.

* * * * *